United States Patent [19]

Walker et al.

[11] Patent Number: 4,718,935

[45] Date of Patent: Jan. 12, 1988

[54] METHOD FOR THE PREPARATION OF MYCOHERBICIDE-CONTAINING PELLETS

[75] Inventors: Harrell L. Walker, Ruston; William J. Connick, Jr., New Orleans, both of La.; Paul C. Quimby, Jr., Leland, Miss.; Harrell L. Walker, Ruston; William J. Connick, Jr., New Orleans, both of La.; Paul C. Quimby, Jr., Leland, Miss.

[73] Assignee: The United States of America as represented by the Secretary of Agriculture, Washington, D.C.

[21] Appl. No.: 773,264

[22] Filed: Sep. 6, 1985

Related U.S. Application Data

[63] Continuation-in-part of Ser. No. 506,952, Jun. 22, 1983, abandoned.

[51] Int. Cl.[4] ...................... A01N 63/04; A01N 37/18

[52] U.S. Cl. .......................................... 71/79; 71/118; 71/DIG. 1; 424/93

[58] Field of Search ..................... 71/79, DIG. 1, 118; 424/93

[56] References Cited

U.S. PATENT DOCUMENTS

| | | | |
|---|---|---|---|
| 2,441,729 | 5/1948 | Steiner | 71/79 |
| 3,649,239 | 3/1972 | Mitchell | 71/63 |
| 3,849,104 | 11/1974 | Daniel et al. | 71/79 |
| 3,999,973 | 12/1976 | Templeton | 71/79 |
| 4,053,627 | 10/1977 | Scher | 424/278 |
| 4,390,360 | 6/1983 | Walker | 71/79 |
| 4,401,456 | 8/1983 | Connick, Jr. | 71/79 |
| 4,419,120 | 12/1983 | Walker | 71/79 |

FOREIGN PATENT DOCUMENTS

| | | | |
|---|---|---|---|
| 0097571 | 1/1984 | European Pat. Off. | 424/93 |
| 1942161 | 2/1970 | Fed. Rep. of Germany | 424/93 |

OTHER PUBLICATIONS

Jung et al, *Chemical Abstract,* vol. 97 #71457t, 1982, "Polymer-entrapped Rhizobum as an Inoculant for Legumes."

H. Lynn Walker; "Factors Affecting Biological Control of Spurred Anoda(*Anoda cristata*)"; Weed Science, vol. 29:505–507(1981).

H. Lynn Walker; "*Fusarium lateritium: A Pathogen of Spurred Anoda (Anoda cristata*), Prickly Sida (*Sida spinosa*), and Velvetleaf (*Abutilon theophrasti*)"; Weed Science, 1981, vol. 29:629–631.

H. L. Walker; "Granular Formulation of *Alternaria macrospora* for Control of Spurred Anoda(*Anoda cristata*)"; Weed Science, vol. 29, No. 3, May 1981, pp. 342–345.

H. L. Walker; "Biocontrol of Sicklepod with *Alternaria Cassiae*"; Proceedings, Southern Weed Science Society, vol. 36, p. 139, 1983.

*Primary Examiner*—Glennon H. Mollrah
*Assistant Examiner*—Raymond Covington
*Attorney, Agent, or Firm*—M. Howard Silverstein; David G. McConnell; Raymond C. Von Bodungen

[57] ABSTRACT

This invention relates to alginate gel pellets containing living fungus capable of producing conidia when exposed to sufficient light and moisture. Fungi are selected and grown for sufficient time to produce inoculum. The fungus cultures are harvested and homogenized for approximately 30 seconds and diluted to a ratio of about 1:3 (v/v) with 1.33% (w/v) sodium alginate in distilled water producing a final concentration of 1.0% sodium alginate and pH of 6.6 to 7.3. Pelletization is then accomplished by dropwise addition into 0.25M $CaCl_2$ in water. The resultant alginate gel pellets of approximately 3 to 5 mm in diameter can then be dried and used to inoculate agriculture fields to kill selected weeds.

5 Claims, No Drawings

METHOD FOR THE PREPARATION OF MYCOHERBICIDE-CONTAINING PELLETS

CROSS-REFERENCE TO RELATED APPLICATIONS

This is a continuation-in-part of application Ser. No. 506,952, filed June 22, 1983,

BACKGROUND OF THE INVENTION (1.) Field of the Invention

This invention relates to a means of mass production and formulation of inoculum of microorganisms. (2.) Description of the Prior Art The merits for using plant pathogens to control weeds in annual crops have been discussed previously for two Colletotrichum spp.(Daniel, et al., U. S. Patent No. 3,849,104 and Templeton, U. S. Pat. No. 3,999,973). The anthracnose fungus *Collebotrichum gloeosporioides* has been used to control the weed northern jointvetch, and other strain of this fungus has been used to control winged waterprimrose. *Colletotrichum malvarum* has been used to control prickly sida. Pathogens have been combined to control several target weeds at once. In other work the fungus *Alternaria macrospora* (American Type Culture Collection No. 42770) has been used to control spurred anoda (H. L. Walker, 1981. Weed Science, Vol. 29, pp. 505-507). *Fusarium lateritium* has been proposed as a biocontrol agent for spurred anoda, prickly sida, and velvetleaf (H. L. Walker, 1981. Weed Science 29:629-631 and U.S. Pat. No. 4,419,120. *Alternaria cassiae* has been used to control sicklepod, coffee senna, and showy crotalaria (H. L. Walker, 1982. Plant Disease 6:426-428 and U. S. Pat. No. 4,390,360.

The effective use of pathogens as microbial herbicides is dependent upon the mass production of inoculum so that periodic applications can be made to the target weeds. Formulation and application methods often are of paramount importance in determining the effectiveness of certain pathogens. Previously reported results indicate that granular formulations of some pathogens have potential as inoculum for weed control in row crop environments (H. L. Walker, 1981. Weed Science 29:342-345); however, the vermiculite carrier utilized in these formulations has the undesirable characteristics of bulkiness, nonuniformity in size, and the granules are easily washed away by rainfall.

The use of alginate gel technology to formulate agricultural products, pesticides, and food items has been disclosed. For example, U.S. Pat. No. 4,053,627 describes the use of alginate gel discs for mosquito control, U.S. Pat. No. 3,649,239 discloses fertilizer compositions, and U.S. Pat. No. 2,441,729 teaches the use of alginate gels as insecticidal as well as candy jellies. In addition, Connick, Jr., U.S. Pat. No. 4,401,456 and 4,400,391 disclose processes for preparing alginate gel beads containing bioactive materials. None of the prior art teaches the use of living fungi as an active material incorporated in an alginate matrix.

SUMMARY OF THE INVENTION

Pelletization of infective propagules of plant pathogens using aqueous solutions of sodium alginate and calcium chloride is disclosed. The granular formulations of pathogens produced have an extended shelf life and sustained release or sustained-production characteristics.

Alginate gel pellets containing living biocontrol fungus are produced as follows: Select and grow the fungus for sufficient time to be used as inoculum; harvest and homogenize living fungal cultures for sufficient time to uniformly mix the fungal fragments. The fungus homogenate is diluted with sodium alginate solution to a sufficient concentration to effect adequate gelation. This product is then added dropwise to a solution of $CaCl_2$ of sufficient concentration in water to form alginate gel pellets which contain living fungus dispersed throughout. These pellets may be dried and, when exposed to sufficient light and moisture, produce fungus conidia. When used in an agricultural environment, a pre-selected fungus can be targeted to control specific weeds.

U.S. Pat. Nos. 4,053,627 and 2,441,729 teach away from use of water soluble and highly ionized salts such as chloride to prepare alginate gels. It is a disadvantage of the processes of these inventions that gel formation is so slow that molds are needed to contain mixtures until the gels set. These patents are silent on the preparation of small pellets or on incorporaiton of fungi. The process of the present invention is not limited by slow gel formation, or by the need to use molds.

U.S. Pat. No. 3,649,239 describes formulations for soil treatment with fertilizers. It does not teach on the preparation of pellets or the use of fungi.

U.S. Pat. Nos. 4,401,456 and 4,400,391 teach processes for incorporating chemical bioactive materials in alginate gels. Terminology, such as herbicide, used in these patents are directed solely from a chemical point of view. Therefore, when considering the teachings of these patents in their entirety and within the scope of their context, one skilled in the art would only be led away from the instant invention because they are directed to kill or eliminate living plants or organisms.

There is no teaching in said patents on, nor is there anticipated, the incorporation of living fungi as active materials. Indeed, one skilled in the art would expect the fungi to die or become ineffective as a result of being incorporated in alginate pellets. The chemical bioactive materials of said patents are released from the products by virtue of their water solubility (leaching or diffusion) or as a result of biodegradation of the alginate matrix. This is totally different from the growth and release of infective propagules from a living fungus.

It was completely unexpected that a living fungus could be incorporated in alginate gel pellets or granules and survive in sufficient amount to give an effective product. For example, barium chloride and cupric chloride are among the preferred water-soluble metal salt gellants taught by U.S. Pat. Nos. 4,401,456 and 4,400,391 for use with chemical bioactive materials, but these salts are fungitoxic when used in the process of the present invention. Other reasons why it is not obvious to use the teachings of U.S. Pat. Nos. 4,401,456 and 4,400,391 to produce effective mycoherbicide pellets are stated below.

The effectiveness of microbial herbicides pelletized in sodium algiante could not be assumed because infective propagules of the pathogens must be free of the gel matrix before they can be disseminated to the target weeds. The fungi grow through the matrix to the surface of the pellets, where spores of the fungi are produced that are free of the alginate gel matrix. This characteristic of the formulations was impossible to identify before development of this process. In no other prior art has this method of formulation of fungi been described. Therefore, this process represents new art.

The stability of the pathogens in air-dried pellets or granules is non-obvious. Other contaminant microorganisms are also pelletized along with the microbial herbicides during this formulation process. Since many microorganisms are capable of competing with the weed pathogens, the recovery and growth of the weed pathogens after storage in the pellets is impossible to predict beforehand.

Spores of the pycnidium-forming fungi are difficult to produce in large quantities. This is because these fungi ust first produce pycnidia before spores (conidia) can be produced inside the pycnidial structure. The formation of pycnidia on the surface of the pellets provides a means to mass produce this group of fungi that has thus far been largely ignored as potential mycoherbicides. Therefore, such use of the alginate pelletization process could hardly be considered obvious.

Pathogens produce spores on the pellets when exposed to suitable environmental conditions such as light and moisture, and continue to produce spores on pellets for several days. Additional spores can be produced after the pellets are washed with water. This sustained-release or sustained production characteristic of alginate pellets was therefore, impossible to predict prior to applicant's discovery.

In addition to its use in mycoherbicide research and and development, the method of sodium alginate formulation described by applicants' preferred embodiment has other applications. For example, the production of inoculum of plant pathogens used for evaluating host resistance of economically important crop species and the formulation of other microbial biocontrol agents may be facilitated by this method.

DESCRIPTION OF THE PREFERRED EMBODIMENTS

Each of five fungi was cultured and pelletized separately to demonstrate the flexibility of the process. The fungi used were *Alternaria macrospora, A. cassiae, Fusarium lateritium, Colletotrichum malvarum,* and a *Phyllosticta sp.* All of these fungi are weed pathogens.

*Fusarium lateritium* Nees ex Fr. and *Alternaria cassiae* Jurair and Khan are on deposit with the USDA-SEA-AR Southern Weed Science Laboratory in Stoneville, Miss.; and with the Agricultural Research Culture Collection (NRRL) in Peoria, Ill., and have been assigned the following accession numbers: NRRL #12552 and NRRL #12553, respectively. Phyllosticta sp is also on deposit as NRRL #15549 *Colletotrichum malvarum* is on deposit as NRRL #15548. The address of the Agricultural Research Culture Collection (NRRL) is: A. J. Lyons, Curator, ARS Patent Collection, Culture Collection Research, NRRC, 1815 N. University St., Peoria, Ill., 61605.

*Colletotrichum malvarum* (A. Braun & Casp.) Southworth has been patented for control of the weed prickly sida (U.S. Pat. No. 3,999,973). *Alternaria macrospora* has been : deposited in the American Type Culture Collection, 12301 Parklawn Dr., Rockville, Md. 20852, ATCC #42770. *A. macrospora* is also included in U.S. Pat. No. 4,419,120.

The fungi were grown in a commercial fermentor in 14-L vessels containing 10 L of growth medium. Actively-growing shake cultures of mycelium 48 to 72 h old, were used as inoculum for the cultures grown in the fermentor. The mycelium and growth medium from the fermentor-grown cultures were harvested 24 to 48 h after inoculation, and homogenized for 30 sec in a commercial blender. This mycelial homogenate was diluted 1:3 (v/v) with 1.33% (w/v) sodium alginate in distilled water to give a total of 4 parts by volume. This mixture had a final sodium alginate concentration of 1.0% and a pH of 6.6 to 7.3. The final pH remained approximately 7.0 when 10% (w/v) kaolin was added to the mycelial homo- genate-alginate mixture. These mixtures with and without kaolin were pelletized by dropwise addition to 0.25 M $CaCl_2$ in distilled water.

Any growth medium in which the desired microorganisms will grow can be used. One that is particularly useful consists of corn meal (15g/L), soybean flour (15g/L), sucrose (30g/L), and calcium carbonate (3g/L) made up to the desired volume with distilled water.

Sodium alginate is the preferred alginate but other water soluble salts of alginic acid such as potassium alginate may be used. Sodium alginate concentration in the mycelial homogenate-sodium alginate-water mixture can be from 0.5 to 2.0% (w/v) but the preferred concentration is 0.75 to 1.0%.

Metal cations that react with and cause gelation of sodium alginate solutions are, for example, the cations of calcium, barium, zinc, copper, aluminum, and mixtures of these. A water soluble calcium salt such as calcium chloride is preferred for the process of this invention because this compound is not toxic to the fungi. An effective concentration range of calcium chloride gellant bath, also called the salt solution, is 1% to 15% (w/v) but, 2% to 5% is preferred. Gelation proceeds faster as the concentration of the salt solution is increased.

Various organic and inorganic fillers such as clays, talc, diatomaceous earth, or sand can be used in the formulations of the present invention. Kaolin is particularly useful in quantities up to about 20% (w/v). Other adjuvants that may be of use when incorporated in formulations are selective fungistats, antibiotics, nutrients, materials that stimulate spore production, viscosity modifiers, materials to control hardness of the pellets or their rate of biodegradation or disintegration and materials that would cause the pellets to float when applied to an aqueous environment.

The simplicity of the requirements for carrying out the process of the present invention permits much latitude in equipment design. A suitable apparatus, described only for the purpose of illustration and not to be construed as limiting the invention, consists of a reservoir to contain the alginate-mycelial mixture, a pump to feed this mixture, or a gravity-feed arrangement, from the reservoir to orifices about 1–2 mm in diameter that permit the mixture to be added in a dropwise manner into a gellant solution contained in any convenient vessel. The alginate gel pellets that form have the fungus mycelium incorporated throughout and are harvested from the gellant solution by any suitable means. A continuous process is possible involving the continuous removal of gel pellets and maintenance of an effective gellant solution concentration. It is also possible to extrude the alginate-mycelial mixture into the gellant solution to form a string-like gel which could be further processed to make granules.

Most mycoherbicides should be processed below about 50° C., preferably in the range of 15°–40° C. Dwell time of the gel pellets in the gellant solution can be from about 0.1 to 15 min, but 0.2 to 5 min is preferred.

Conidia were produced on the surface of the pellets when freshly prepared pellets were exposed for 10 min to light supplied by three 275-W sunlamps that were suspended above the trays. A small fan dissipated the heat generated by the sunlamps. The pellets were exposed to three additional light treatments at 12-h intervals, and then allowed to air dry.

Freshly prepared pellets can be used for mass production of spores or can be air dried or freeze dried immediately after formulation and stored for future use. When the dried pellets are rewetted and exposed to light, the fungi produce conidia.

All of the pelletized fungi sporulated profusely on the surfaces of the pellets (Tables 1 and 2).

Mycelia formulated in this manner can produce conidia for at least 7 to 9 days when subjected to conditions conducive to sporulation. This sustained-release characteristic could provide residual activity to enhance the performance of mycoherbicides. Similar results were obtained for formulations with and without kaolin that were stored at ambient conditions or 4° C. for 6 to 8 months. Therefore, the preferred embodiment of applicants' invention also provides an improved method for storing inoculum for extended periods of time.

The procedure of drying the pellets immediately after pelletization simplifies the large-scale production of some pathogens used as mycoherbicides by eliminating the sporulation requirements during the formulation and packaging process. Field observations confirmed that the pathogens used in this study, when formulated and packaged as dried pellets without conidia, sporulated readily under field conditions, provided adequate moisture was present.

Only a few pycnidium-forming fungi have been studied as potential mycoherbicides, due partially to problems involving inoculum production. In these studies the Phyllosticta sp. produced numerous pycnidia on the pellets (Tables 1 and 2). The pycnidium-forming fungi appear to be ideally suited for this method of formulation, because in this method the conidia need not be removed from the pycnidia for field application and the pycnidia would help protect the conidia from adverse environmental conditions.

Alginate formulations of mycoherbicides can be applied directly to soil as pellets, or conidia can be produced on the pellets, then extracted and applied as foliar sprays. Methods have been developed for the pelletization of herbicides as floating or sinking granules for control of aquatic weeds, and these adaptations are of value in the formulation of mycoherbicides.

TABLE 1

Assay of conidia produced by fungi pelletized in alginate[1].

| Fungus | Assay species (weeds)[2] | Conidia ($\times 10^6$)/g formulation |
|---|---|---|
| *Alternaria cassiae* | *Cassia obtusifolia* L. | 5[3] |
| *Alternaria macrospora* | *Anoda cristata* (L.) Schlecht. | 7[3] |
| *Fusarium lateritium*[5] | *Abutilon theophrasti* Medic. | 14[4] |
| *Colletotrichum malvarum* | *Sida spinosa* L. | 12[4] |
| Phyllosticta sp. | *Sorghum halepense* (L.) pers. | 5,000[4] |

[1]Mycelia were pelletized without kaolin and induced to sporulate immediately after formulation. One liter of mycelium and growth medium produced approximately 72 g of air-dried product. Each value is the average for three replications.
[2]Conidia of all fungi were infective and 95 to 100% viable.
[3]Pellets were air-dried 48 h after formulation.
[4]Pellets were air-dried 96 h after formulation.
[5]Macroconidia of this fungus were used.

TABLE 2

Number of conidia collected in single and multiple harvests from alginate-kaolin formulations[1].

| Fungus | Condia ($\times 10^6$)/g formulation[2] Time (days) of harvest after rewetting 2 | 5 | 7 | 9 | Total | Single harvest[3] |
|---|---|---|---|---|---|---|
| *Alternaria cassiae* | 0.58 | 0.59 | 0.20 | 0.07 | 1.5 | 0.64 |
| *Alternaria macrospora* | 0.92 | 0.88 | 0.44 | 0.22 | 2.4 | 1.40 |
| *Fusarium lateritium*[4] | 4.2 | 3.4 | 1.3 | 0.66 | 9.6 | 13.0 |
| *Colletotrichum malvarum* | 0.86 | 3.8 | 3.5 | 3.1 | 11.3 | 28.0 |
| Phyllosticta sp. | 300 | 180 | 22.7 | 18.0 | 520 | 580 |

[1]Mycelia were pelletized in sodium alginate and kaolin, air dried immediately, and stored at 4 C. for approximately 10 wk. One liter of mycelium and growth medium produced approximately 472 g of air-dried product. Each value is the average for three replications.
[2]The same samples of the formulations were rewetted and induced to sporulate after each harvest. No conidia were present initially.
[3]A single harvest of conidia was made 9 days after rewetting.
[4]Macroconidia were counted.

EXAMPLE 1

*Alternaria cassiae* was grown in a commercial fermentor in 14-L vessels containing 10 L of growth medium. Actively-growing shake cultures of mycelium,48 to 72 h old, were used as inoculum for the cultures grown in the fermentor. The mycelium and growth medium from the fermentor-grown cultures were harvested 24 to 48 h after inoculation, and homogenized for 30 sec in a commercial blender.

This mycelial homogenate was diluted 1:3 (v/v) with 1.33% (w/v) sodium alginate in distilled water. This mixture had a final sodium alginate concentration of 1.0% and a pH of 6.6 to 7.3. These mixtures were pelletized by dropwise addition to 0.25 M $CaCl_2$ in distilled water.

The apparatus used to produce pellets of uniform size from a measured volume of alginate-mycelial mixture consisted of a reservoir for the mixture, a peristaltic pump, a heating coil that was submersed in a water bath, needle valves and pipet tips that were cut from 1-ml polystyrene, disposable pipets and mounted through holes drilled in a sheet of acrylic plastic. The flow rate was regulated by adjusting the rpm of the pump and by the needle valves so that the alginate-mycelial mixture dripped into a 2-L reservoir containing the salt solution. The heating coil warmed the mixture to 40° C. to help maintain a constant viscosity. Alginate gel pellets, 3 to 4 mm in diameter containing the fungus dispensed throughout, were formed as the droplets contacted the salt solution and these were harvested with a small dip net. Each pump head was connected to 12 pipet tips, and this arrangement processed the mixture at a rate of 4 L/h.

To produce larger quantities of pellets, another apparatus was used. Each of the five pump heads was connected by silicone tubing to a funnel 12.5 cm in diam. The funnels were inverted and sandwiched between two sheets of acrylic plastic and held in place with bolts and wing nuts. A rubber gasket provided a seal between the funnels and the bottom sheet of acrylic plastic that had holes 2 mm in diameter drilled in a 23 mm grid pattern. This apparatus processed 1 L/min of the mycelial-alginate mixture; however, the volume of processed mixture could not be precisely controlled as with the apparatus previously described. The pellets (3 to 5 mm in diameter) were harvested from the salt solution, rinsed in distilled water, and spread one layer deep into fiberglass trays (130 by 260 cm) to air dry.

One liter of mycelium and growth medium produced approximately 72 g of air-dried product. These preparations produced approximately $5 \times 10^6$ conidia per gram of formulation. The conidia were 95 to 100% viable and infective.

EXAMPLE 2

*Fusarium lateritium* was pelletized as described in Example 1. These preparations produced $14 \times 10^6$ macroconidia per gram of formulation. These spores were infective and 95 to 100% viable.

EXAMPLE 3

*Alternaria macrospora* was pelletized as described in Example 1. These preparations produced $7 \times 10^6$ conidia per gram of formulation. These spores were infective and 95 to 100% viable.

EXAMPLE 4

*Colletotrichum malvarum* was pelletized as described in Example 1. These preparations produced $12 \times 10^6$ conidia per gram of formulation. These spores were infective and 95 to 100% viable.

EXAMPLE 5

Using the process described in Example 1, a Phyllosticta sp. was pelletized as a representative genus of the pycnidiumforming fungi. These preparations produced $5 \times 10^9$ conidia per gram of formulation. The spores were infective and 95 to 100% viable.

EXAMPLE 6 as described in Example 1,

*Alternaria cassiae* was prepared except that 10% (w/v) kaolin was added to the mycelial-alginate mixture before pelletization. These preparations produced approximately 472 g of air-dried product per liter of mycelium and growth medium. Approximately $6 \times 10^5$ conidia were produced per gram of formulation, following nine days of light treatments.

EXAMPLE 7

*Fusarium lateritium*, treated as described in Example 6, produced $13 \times 10^6$ conidia per gram of formulation.

EXAMPLE 8

*Alternaria macrospora* formulated as described in Example 6, produced $1 \times 10^6$ conidia per gram of formulation.

EXAMPLE 9

*Colletotrichum malvarum* formulated as described in Example 6, produced $28 \times 10^6$ conidia per gram of formulation.

EXAMPLE 10

A *Phyllosticta* sp. formulated as described in Example 6, produced abundant pycinidia and $58 \times 10^7$ conidia per gram of formulation.

EXAMPLE 11

Each of the five fungi was formulated as described in Examples 6 through 10. The pelleted mycelia were air-dried and stored at 4 C for approximately 10 weeks. Samples containing each fungus were rewetted and exposed to sunlamps to induce sporulation. Each fungus produced spores on the granules in a sustained production manner for nine days following rewetting. These data are summarized in Table 2.

EXAMPLE 12

In field tests of *Alternaria cassiae* for the biological control of sicklepod, granular formulations containing mycelium, sodium alginate, and kaolin prepared as in Example 6, were applied preemergence at a banded rate of 500 kg/ha. *A. cassiae* sporulated readily on the granules and produced approximately 5 kg of conidia/500 kg of formulation. Approximately 50% of the sicklepod plants were controlled within 14 days, resulting in significant soybean yield increases when compared to the yields from the untreated control plots. (H. L. Walker. 1983. Proceedings of Southern Weed Science Society, Vol. 36, p. 139).

We claim:

1. Alginate gel pellets containing living fungus, said pellets comprising effective concentrations of living fungus as the active ingredient dispersed throughout an alginate gel matrix carrier, said fungus selected from the group consisting of *Alternaria cassiae, Fusarium lateritium, Alternaria macrospora, Colletotrichum malvarum* and Phyllosticta sp. NRRL #15549, said fungus targeted to the control of specific weeds.

2. Dried alginate gel pellets of claim 1.

3. Alginate gel pellets of claim 1 including 10% (w/v) kaolin filler material.

4. Alginate gel pellets of claim 1 capable of producing fungus conidia when exposed to sufficient light.

5. Alginate gel pellets of claim 2 capable of producing fungus conidia when exposed to sufficient light and moisture.

* * * * *